(12) United States Patent
Uhri et al.

(10) Patent No.: US 12,349,925 B2
(45) Date of Patent: Jul. 8, 2025

(54) POWERED SURGICAL TOOL WITH AN OSCILLATING SAW BLADE

(71) Applicant: DePuy Synthes Products, Inc., Raynham, MA (US)

(72) Inventors: Patrick Uhri, Reigoldswil (CH); Rolf Schlienger, Rheinfelden (CH); Markus Hermann, Laupersdorf (CH); Stefan Gisler, Wallbach (CH)

(73) Assignee: DePuy Synthes Products, Inc.

( * ) Notice: Subject to any disclaimer, the term of this patent is extended or adjusted under 35 U.S.C. 154(b) by 317 days.

(21) Appl. No.: 18/183,715

(22) Filed: Mar. 14, 2023

(65) Prior Publication Data

US 2024/0307070 A1  Sep. 19, 2024

(51) Int. Cl.
| | | |
|---|---|---|
| A61B 17/14 | (2006.01) | |
| A61B 17/00 | (2006.01) | |
| A61B 34/00 | (2016.01) | |

(52) U.S. Cl.
CPC .......... *A61B 17/142* (2016.11); *A61B 17/144* (2016.11); *A61B 2017/00115* (2013.01); *A61B 2017/00477* (2013.01); *A61B 2017/00876* (2013.01); *A61B 34/76* (2016.02)

(58) Field of Classification Search
CPC ............................ A61B 17/142; A61B 17/144
See application file for complete search history.

(56) References Cited

U.S. PATENT DOCUMENTS

| | | |
|---|---|---|
| D52,707 S | 11/1918 | Boesch |
| 5,382,249 A | 1/1995 | Fletcher |
| 5,507,763 A | 4/1996 | Petersen et al. |
| D406,023 S | 2/1999 | Okada |
| D406,223 S | 3/1999 | Tran |
| 6,022,353 A | 2/2000 | Fletcher et al. |

(Continued)

FOREIGN PATENT DOCUMENTS

| | | |
|---|---|---|
| CN | 302696268 | 12/2013 |
| CN | 307704055 | 12/2022 |

(Continued)

OTHER PUBLICATIONS

DePuy Synthes, Battery Power Line II Instructions for Use, 2015.

(Continued)

*Primary Examiner* — Christian A Sevilla
(74) *Attorney, Agent, or Firm* — Troutman Pepper Locke LLP

(57) ABSTRACT

In general, devices, systems, and methods for assembly and operation of a handheld oscillating surgical saw are provided. In exemplary embodiments, a surgical tool includes a handpiece comprising a coupling head that includes a slot and a magnet, the slot being configured to releasably receive a surgical saw blade configured to cut bone, and the magnet being configured to magnetically attract the saw blade, wherein the coupling head is configured to move between a first position, in which the slot has a first height and the coupling head is configured to selectively receive the surgical saw blade therein and release the surgical saw blade therefrom, and a second position, in which the slot has a second height that is less than the first height and the coupling head is configured to fixedly seat the saw blade therein.

20 Claims, 14 Drawing Sheets

(56) References Cited

U.S. PATENT DOCUMENTS

| | | | |
|---|---|---|---|
| D448,634 S | 10/2001 | Hickman | |
| 7,744,616 B2 | 6/2010 | O'Donoghue | |
| D686,049 S | 7/2013 | Ji | |
| D686,470 S | 7/2013 | Ji | |
| D706,099 S | 6/2014 | Neitzell et al. | |
| 8,852,221 B2 * | 10/2014 | Boykin | A61B 17/142 606/171 |
| 8,920,424 B2 * | 12/2014 | Boykin | B27B 33/02 606/82 |
| D742,002 S | 10/2015 | Fisher et al. | |
| D862,185 S | 10/2019 | Dai | |
| D955,834 S | 6/2022 | Haight et al. | |
| 2002/0116023 A1 | 8/2002 | Fletcher et al. | |
| 2003/0014067 A1 | 1/2003 | Kullmer et al. | |
| 2003/0199880 A1 * | 10/2003 | Meckel | A61B 17/142 606/82 |
| 2004/0098000 A1 | 5/2004 | Kleinwaechter | |
| 2004/0199167 A1 | 10/2004 | Fletcher et al. | |
| 2005/0113840 A1 * | 5/2005 | Metzger | A61B 17/157 606/88 |
| 2005/0192585 A1 * | 9/2005 | Simmons | B23D 51/16 606/82 |
| 2006/0206100 A1 * | 9/2006 | Eskridge | A61B 17/142 606/1 |
| 2007/0119055 A1 | 5/2007 | Walen et al. | |
| 2014/0163558 A1 | 6/2014 | Cosgrove et al. | |
| 2019/0290289 A1 | 9/2019 | Schmuckli et al. | |
| 2020/0001494 A1 | 1/2020 | Gisler et al. | |
| 2021/0113215 A1 | 4/2021 | Gisler | |
| 2021/0353303 A1 | 11/2021 | Gayle | |
| 2023/0013089 A1 | 1/2023 | Gisler | |
| 2023/0082586 A1 | 3/2023 | Lindemann et al. | |
| 2023/0263534 A1 | 8/2023 | Kowall et al. | |
| 2024/0198441 A1 | 6/2024 | Rubens et al. | |

FOREIGN PATENT DOCUMENTS

| | | |
|---|---|---|
| EP | 2647339 B1 | 4/2020 |
| KR | 300960755 | 6/2018 |
| KR | 300987942 | 1/2019 |

OTHER PUBLICATIONS

DePuy Synthes, Battery Power Line II User's Manual, May 2021.
DePuy Synthes, Saw Blades, 2023 (available at <https://www.jnjmedtech.com/en-us/products/power-tools/saw-blades>).
Komet Medical, Powered Instruments Catalog, Jan. 2023.
International Search Report and Written Opinion for PCT Patent Application No. PCT/IB2024/052117 mailed Jun. 4, 2024. (17 pages).
U.S. Appl. No. 29/872,520, filed Mar. 14, 2023, Patrick Uhri et al.
U.S. Appl. No. 29/872,523, filed Mar. 14, 2023, Patrick Uhri et al.
"10PCS Titanium Multitool Blades" Nov. 19, 2022, Amazon, site visited Jul. 16, 2024: https://www.amazon.com/Titanium-Oscillating-Multitool-Material-Milwaukee/dp/B0BMXKV6L6.
"6-Inch 14TP1 Heavy Duty Metal Cutting Reciprocating Saw Blades" Nov. 12, 2018, Amazon, site visited Jul. 16, 2024: https://www.amazon.com/dp/B07DPPSL4Y.
"Electric Bone Cutting Oscillating Saw" Dec. 30, 2022, Amazon, site visited Jul. 16, 2024: https://www.amazon.com/Electric-Oscillating-Orthopedic-Veterinary-Instrument/dp/B0BRCSR8TF.
"Large Bone Saw Blades Stryker Replacements" 2021, Brasseler USA Medical, site visited Jul. 16, 2024: https://brasselerusamedical.com/wp-content/uploads/sites/8/2022/07/BM_5513_Stryker-Large-Bone-Saw-Blade-Brochure.pdf.
"Stryker sag saw blade" Feb. 9, 2018, YouTube, site visited Jul. 16, 2024: https://www.youtube.com/watch?v=2wfqWOQcmo.

* cited by examiner

POWERED SURGICAL TOOL WITH AN OSCILLATING SAW BLADE

FIELD

The present disclosure relates generally to powered surgical tools with oscillating saw blades.

BACKGROUND

In the field of orthopedics, surgical saws are used to cut bone, often in joint replacement procedures, such as hip replacements and knee replacements. Powered oscillating saws provide higher accuracy and efficiency than traditional manual bone saws. A saw blade is typically operatively coupled to a power source to enable powered oscillation of the saw blade, which provides the ability to cut bone. A handpiece of a powered surgical saw generally can be used with a variety of different blades attached, each blade providing a differing geometry that may be useful in different surgical applications. However, it can be difficult for a physician or other medical professional to change blades in a safe manner. Ensuring that the blade is properly secured in the surgical tool is key to ensuring precise cutting by the tool during a surgical procedure.

Accordingly, there remains a need for improved powered surgical tools with oscillating saw blades.

SUMMARY

In general, devices, systems, and methods for powered surgical tools with oscillating saw blades are provided.

In one aspect, a surgical tool is provided that in one implementation includes a handpiece comprising a coupling head that includes a slot and at least one magnet, the slot being configured to releasably receive a surgical saw blade configured to cut bone, and the at least one magnet being configured to magnetically attract the saw blade, wherein the coupling head is configured to move between a first position, in which the slot has a first height and the coupling head is configured to selectively receive the surgical saw blade therein and release the surgical saw blade therefrom, and a second position, in which the slot has a second height that is less than the first height and the coupling head is configured to fixedly seat the saw blade therein.

The surgical device can have any number of variations. For example, the coupling head can include a movable lid configured to be in an upward position with the coupling head in the first position and in a downward position with the coupling head in the second position. Further, the tool can include an actuator configured to be actuated to selectively cause the lid to move between the upward and downward positions. The lid of the tool can include at least one male member extending therefrom that is configured to, with the coupling head in the second position, engage at least one corresponding female member formed in the saw blade.

For another example, the tool can include an actuator configured to be actuated to selectively cause the coupling head to move between the first and second positions.

For still another example, the slot can be defined by a bottom surface, a top surface, a left sidewall, a right sidewall, and a distal-facing surface, the at least one magnet can be positioned at the distal-facing surface, and the saw blade can be configured to extend distally out of the slot. Further, the top surface can be defined by a lid configured to be movable relative to the distal-facing surface to move the coupling head between the first and second positions.

For another example, the coupling head moving into the second position from the first position can be configured to provide feedback to a user indicative of the saw blade being fixedly seated therein, the feedback including at least one of visual feedback, audible feedback, and haptic feedback. Further, when the feedback includes at least the visual feedback, the tool can also include the saw blade, and the saw blade can include an alignment feature configured to align with the coupling head with the coupling head being in the second position. Further, when the feedback includes at least the audible feedback, the tool can include the saw blade and magnetic engagement of the saw blade and the at least one magnet can be configured to provide the audible feedback. Further, when the feedback includes at least the haptic feedback, the tool can include the saw blade and an interaction between a magnetic field produced by the at least one magnet and the saw blade can be configured to provide the haptic feedback.

For still another example, the tool can include the sawblade and the at least one magnet can include a first magnet and a second magnet, the saw blade can include a U-shaped proximal portion including first and second arms, and with the coupling head in the second position, the first arm can be positioned adjacent to the first magnet and the second arm can be positioned adjacent to the second magnet.

In another aspect, a surgical method is provided that can include inserting a surgical saw blade into a slot formed between a base and a lid of a coupling head of a surgical tool, sliding the saw blade proximally into the slot until the saw blade contacts a distal wall of the base and engages at least one magnet at the distal wall, and closing the lid of the coupling head and thereby securing the saw blade to the coupling head.

The method can vary in any number of ways. For example, the saw blade engaging the at least one magnet can provide at least one of visual, audible, and haptic feedback to a user.

For another example, closing the lid of the coupling head can include clamping the lid on the saw blade.

For still another example, closing the lid can include actuating an actuator of the surgical tool that causes the lid to move relative to the base.

For another example, closing the lid can include engaging at least one male member extending from the lid with at least one corresponding female member formed in the saw blade. Further, the method can include, after closing the lid, actuating the actuator again, thereby causing the lid to move relative to the base, and then removing the saw blade from the slot. In some instances, the saw blade cannot be removed from the slot until the actuator is actuated again.

In still another example, the method can include, with the saw blade secured to the coupling head, oscillating the saw blade relative to bone.

BRIEF DESCRIPTION OF DRAWINGS

The present invention is described by way of reference to the accompanying figures which are as follows.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

In general, devices, systems, and methods for assembly and operation of a handheld oscillating surgical saw are provided. In an exemplary implementation, a saw head of a handheld oscillating surgical saw includes a coupling head configured to receive and retain a saw blade inserted in a slot therein regardless of whether the coupling head is in an open or in a closed position. The coupling head includes a plurality of magnets configured to magnetically retain the saw blade in the slot of the coupling head. The coupling head is configured to magnetically retain the saw blade in the coupling head regardless of the orientation of the handheld oscillating surgical saw (e.g., with a tip of the saw blade pointing downward). This magnetic retention reduces the likelihood that the saw blade comes loose from the saw head prior to the coupling head being secured in the closed position which locks the saw blade in place.

Figure 1:
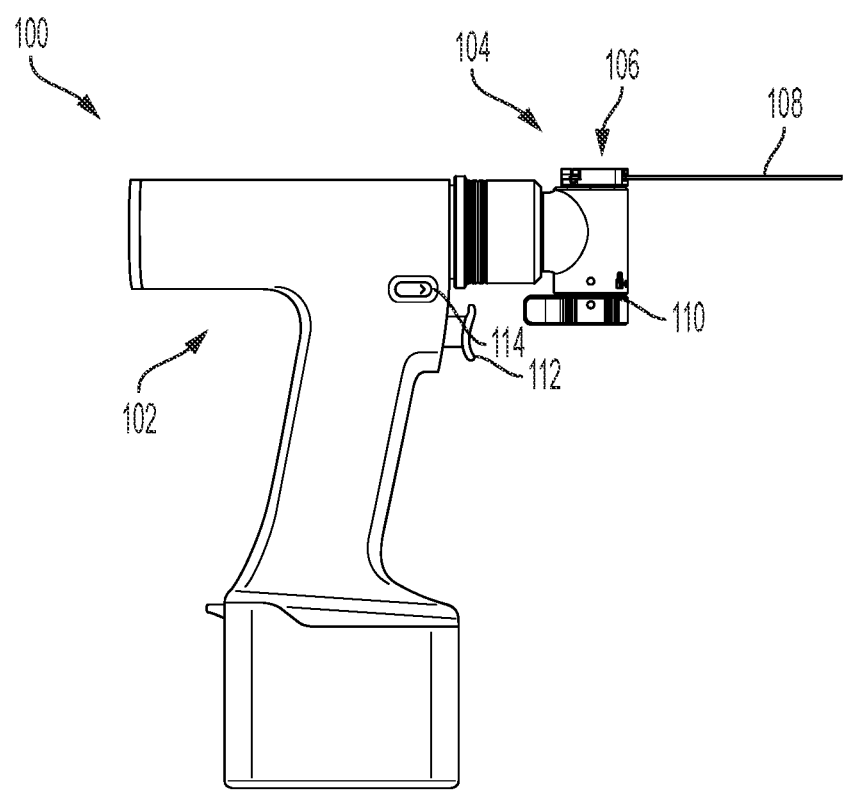
FIG. 1 is a perspective view of a handheld oscillating saw tool.

FIG. 1 illustrates an embodiment of a handheld oscillating surgical saw 100. The surgical saw includes a handpiece 102 configured to be held by a user. The handpiece has a saw head 104 configured to receive a saw blade 108. In the illustrated embodiment, the saw head 104 is fixedly attached to the handpiece 102. However, in alternative embodiments, a saw head and a handpiece may be separable from one another. The saw head 104 includes a coupling head 106 which retains the saw blade 108 in a slot therein (e.g., slot 308 shown in FIG. 3). The saw head 104 also includes an actuator, here a knob 110, which is operatively coupled to the coupling head 106 to lock the saw blade 108 in position for operation of the handheld oscillating surgical saw 100. The knob 110 rotates 120 degrees to move the coupling head between an unlocked position and a locked position. This operative coupling is described in more detail with respect to FIG. 10 and FIG. 14, below. In some embodiments, the knob may be substituted for another form of actuator, for example, a lever, a button, etc.

To operate the handheld oscillating surgical saw 100, a user actuates a second actuator, e.g., trigger 112, and the saw blade 108 oscillates back and forth along a 4.5 degree arc. The trigger 112 is operatively coupled to a controller and a motor in the handpiece 102. As the trigger 112 is pressed, a signal is transmitted to the controller, which controls the operating speed of the motor, and thereby the oscillation rate of the saw blade 108. The trigger 112 has 10 mm of travel and movement of the trigger 112 is proportional to the speed of oscillation of the saw blade 108. A mode switch 114 on a side of the handpiece 102 is a sliding lock that locks the trigger 112 and prevents accidental activation of the motor of the device and therefore the saw blade 108.

The handpiece 102 and/or the saw head 104, as well as other embodiments of oscillating saw tools described herein, can be formed from a rigid biocompatible material, such as stainless steel, titanium, or other material. The rigid biocompatible material may provide durability over the course of experiencing vibrations due to the oscillating saw blade 108 in the performance of one or more surgical procedures.

Figure 2:
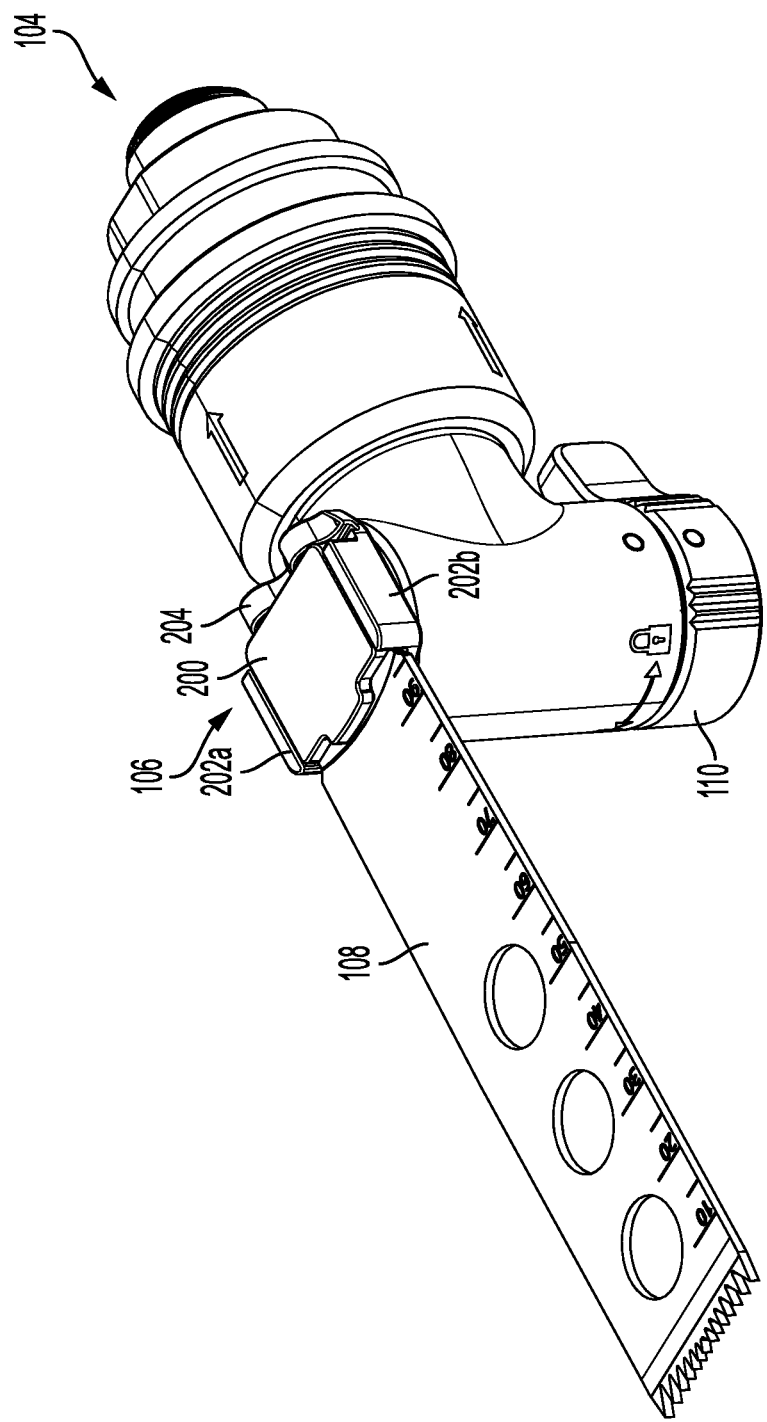
FIG. 2 is a perspective view of a saw head and saw blade of the handheld oscillating saw tool of FIG. 1.

FIGS. 2-5 illustrate one embodiment of a saw head 104 of the handheld oscillating surgical saw 100 of FIG. 1. As shown in FIG. 2, the saw head 104 is configured to be coupled to the saw blade 108 via coupling head 106. The coupling head 106 includes a slot 308 (shown in FIG. 3) which is defined by sidewalls 202a, 202b, magnet housing 204, and bottom surface 306 (also shown in FIG. 3). The sidewalls 202a, 202b, the magnet housing 204, and the bottom surface 306 form a base of the coupling head 106.

The base of the coupling head 106 is covered by lid 200 which includes a stem 602 (shown in FIG. 6) that extends through the slot and downward toward knob 110. The spacing between the lid 200 and the base of the coupling head 106 forms the slot. The lid 200 is moveable between a first position and a second position. In the first position, the spacing between the lid 200 and the bottom surface 306 provides clearance for the coupling portion 302 of the saw blade to slide therebetween. In the second position, the lid 200 is lowered toward the base of the coupling head 106 to clamp the saw blade 108 between the lid 200 and the base of the coupling head 106.

Figure 3:
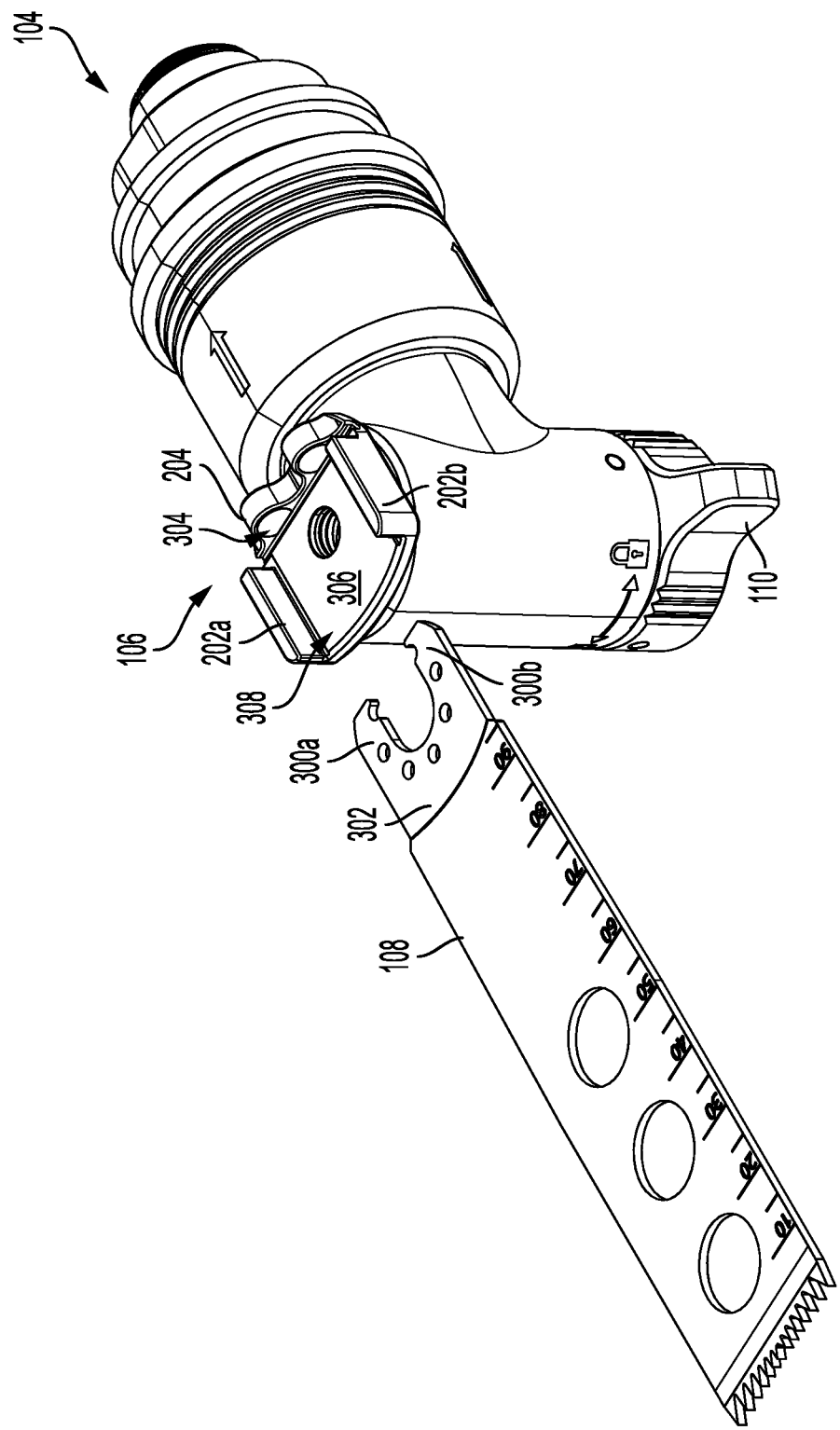
FIG. 3 is a perspective view of the saw head and saw blade of the handheld oscillating saw tool of FIG. 1 with a lid of a coupling head of the saw head removed.

FIG. 3 illustrates an embodiment of the saw head 104 wherein the lid 200 (shown in FIG. 2) has been removed for ease of viewing the slot 308 and other features of the coupling head 106. In FIG. 3, the saw blade 108 is positioned outside of the slot 308. The saw blade 108 includes a coupling portion 302 that is insertable into the coupling head 106. The coupling portion 302 of the saw blade 108 is generally U-shaped with arms 300a, 300b. In some embodiments, the coupling portion 302 is thinner than the remainder of the saw blade.

The saw blade 108 has a cutting portion 310 with teeth 312 at a distal end thereof. The cutting portion 310 of the saw blade 108 of the embodiment of FIG. 3 is generally rectangular in shape. In other embodiments, the saw blade can have any number of different structural configuration (e.g., shape, length, size). By way of example, in some aspects, the saw blade can have a substantially rectangular-shaped body, whereas in other aspects, the blade can have a substantially triangular shaped body (e.g., a fan-shape, such as a radial projection extending outward from the coupling portion such that the teeth of the saw blade are positioned along an arc-shaped distal portion). A person skilled in the art would appreciate that the saw blade can have other suitable shapes.

In the embodiment of FIG. 3, the slot 308 is generally shaped like a rectangular prism and is configured to receive a coupling portion 302 of the saw blade 108 that includes arms 300a, 300b. The sidewalls 202a, 202b are generally parallel to one another and perpendicular to a surface 304 of the magnet housing 204 to form this rectangular shape. A bottom surface 306 extends between the sidewalls 202a, 202b and the surface 304 of the magnet housing 204 and forms a bottom of the slot 308. The slot 308 is configured to accommodate varying thicknesses of saw blade 108, for example, blades with thicknesses of between 0.4 and 1.47 mm at the coupling portion 302. The slot 308 opens to a height of 1.75 mm between the underside of the lid 200 and the bottom surface 306 to provide clearance to insert a saw blade 108.

In some embodiments, the slot 308 may have an alternate shape. For example, sidewalls 202a, 202b may not be parallel to one another. In such an example, the bottom surface 306 may be trapezoidal in shape and sidewalls 202a, and 202b may be closer together at a rear of the slot 308 than at an opening of the slot 308. In such embodiments, the coupling portion 302 may have a similar trapezoidal shape. In another alternative embodiment, at least one of the sidewalls 202a, 202b and/or the surface 304 has a curved shape. In such an alternative embodiment, the coupling portion of the saw blade 108 may have a corresponding curved shape.

Figure 4:
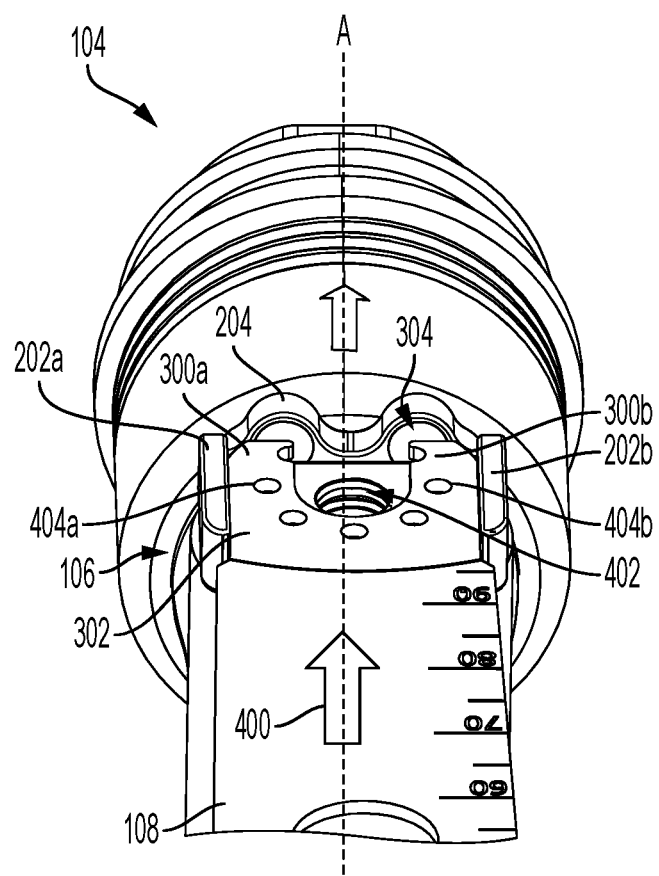
FIG. 4 is another perspective view of the saw head and saw blade of the handheld oscillating saw tool of FIG. 1 with a lid of a coupling head of the saw head removed.

FIG. 4 is a perspective view of the saw head 104 of the handheld oscillating surgical saw 100 of FIG. 1 with the saw blade 108 inserted in the slot. The lid 200 (shown in FIG. 2) is not depicted in FIG. 4 to allow a view inside of the slot 308. With the saw blade 108 inserted in the slot 308, the arms 300a, 300b of the coupling portion 302 of the saw blade 108 contact the surface 304 of the magnet housing 204. In the embodiment of FIG. 4, the magnet housing 204 includes two magnets, each enclosed in a cylindrically-shaped portion of the magnet housing 204. Each of the two magnets in the magnet housing 204 lines up with one of the arms 300a, 300b parallel to an insertion axis A. Upon assembly, generally the lid 200 (shown in FIG. 2) is in position in the coupling head 106 with a stem 602 of the lid (shown in FIG. 6) extending downward into hole 402 in the base of the coupling head 106. As the saw blade 108 is pushed into the slot 308, represented by arrow 400, the arms 300a, 300b proceed into the slot 308 on opposing sides of the stem 602 of the lid 200.

In some embodiments, any appropriate number of magnets may be used to engage the saw blade. For example, one larger magnet may be used in the place of the two cylindrical magnets of the embodiment of FIG. 4. In another example, three or more magnets may be used to retain the saw blade which may have any number of arms.

As the arms 300a, 300b of the saw blade 108 move into the slot 308, the arms 300a, 300b experience the magnetic field created by the magnets in the magnet housing 204. The pull of the magnets on the arms 300a, 300b creates visual, haptic, and/or audible feedback to the user inserting the saw blade 108. In some embodiments, the audible feedback is the sound of the arms 300a, 300b contacting the magnet housing 204. In some embodiments, the haptic feedback is a pull on the saw blade by the magnetic field that is felt by the user inserting the saw blade 108. In some embodiments, the visual feedback is the arms 300a, 300b contacting the surface 304 of the magnet housing 204.

Figure 5:
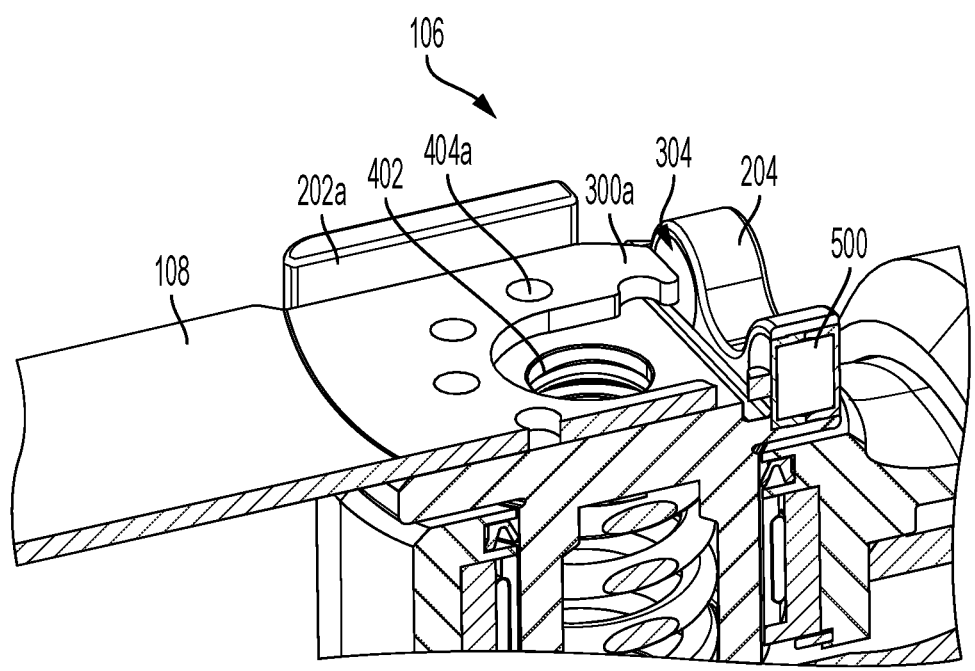
FIG. 5 is a cross-sectional view of the coupling head of the handheld oscillating saw tool of FIG. 1.

FIG. 5 is a cross-sectional view of the coupling head 106 of the saw head 104. The cross-section shows a magnet 500 positioned inside the magnet housing. The magnet 500 is a cylindrically-shaped neodymium magnet and is one of two magnets in the magnet housing 204, each corresponding to a position of an arm 300a, 300b of the saw blade 108 when the saw blade 108 is positioned in the slot 308.

In some embodiments, instead of a magnet housing 204 that contains one or more magnets, the coupling head 106 may include one or more magnets adhered to a wall. In some embodiments, the rear wall of the coupling head may be made of a magnetic material. In some embodiments, the magnets are sized or selected with respect to a thickness or weight of a saw blade.

Figure 6:
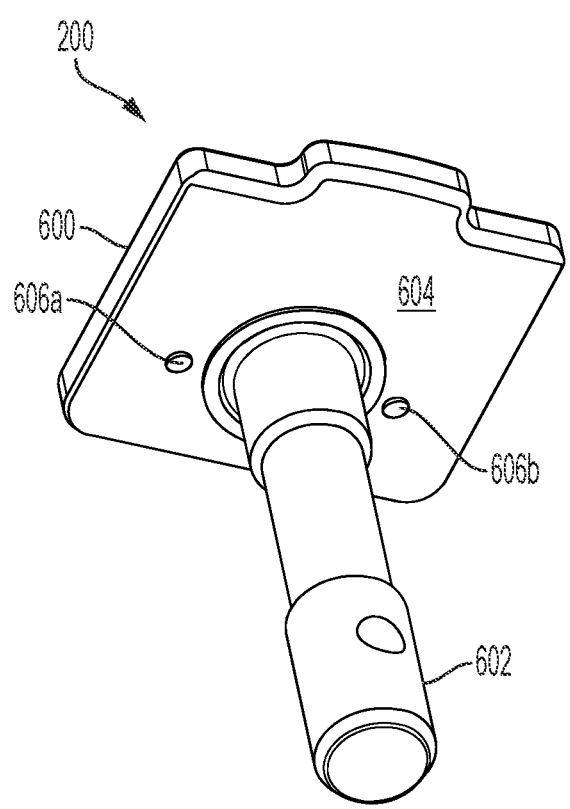
FIG. 6 is a perspective view of a lid of the coupling head of the handheld oscillating saw tool of FIG. 1.

FIG. 6 is a perspective view of the lid 200 of the coupling head 106 of the handheld oscillating surgical saw 100 of FIG. 1. The lid 200 includes a top 600 and a stem 602. When the lid 200 is assembled in the coupling head 106, the stem 602 extends into the hole 402 (shown in FIG. 4) to be secured when the knob 110 is turned. An underside 604 of the lid 200 includes male members 606a, 606b that interfaces with female members 404a, 404b (shown in FIG. 4) on the saw blade 108. The male members 606a, 606b may be, for example, protrusions, pins, etc. The female members may be, for example, notches, holes, etc. In some embodiments, one male member on the lid 200 may interface with one female member on the saw blade 108. In some embodiments, more than one male member on the lid 200 may interface with more than one female member on the saw blade 108. In the embodiment of FIG. 6, male members 606a, 606b positioned on the underside 604 of the lid 200 are configured to interface with female members 706a, 706b of a saw blade 700 shown in FIG. 7.

Figure 7:
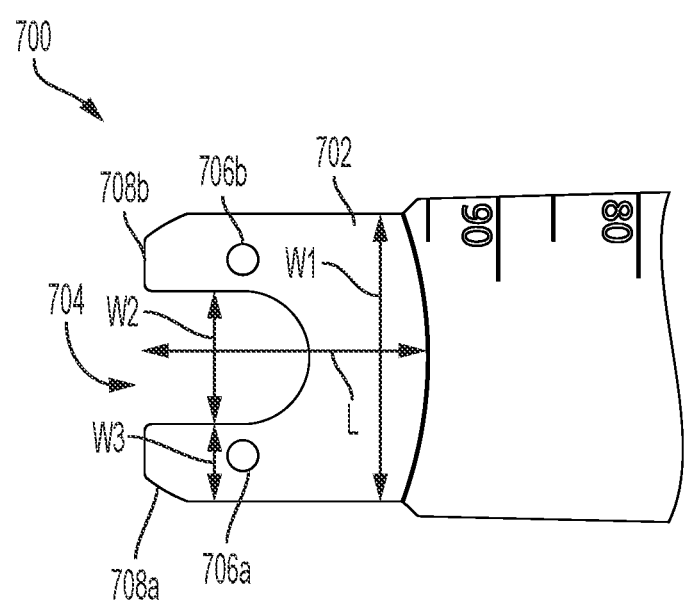
FIG. 7 is a top view of a coupling portion of an embodiment of a saw blade.

FIG. 7 shows a coupling portion of another embodiment of a saw blade 700. The saw blade 700 includes a coupling portion 702. The coupling portion 702 has a U-shaped cutout 704 that forms arms 708a, 708b and is configured to allow the stem 602 of the lid 200 (shown in FIG. 6) to extend therethrough. The coupling portion 702 also includes two female members 706a, 706b which are configured to interface with male members (e.g., male members 606a, 606b shown in FIG. 6) of an underside of a lid (e.g., lid 200 shown in FIG. 6). The pattern of the female members and the male members between a coupling portion of a saw blade and an underside of a lid may or may not match (e.g., matching being each female member on the coupling portion of the saw blade interfacing with a male member on the underside of the lid and not matching being having more female members on the coupling portion of the saw blade than male members on the underside of the lid).

In one embodiment, the coupling portion has a width W1 of 20.5 mm and a length L of 20.2 mm. In this embodiment, the U-shaped cutout 704 has a width W2 of 9.5 mm and each arm 708a, 708b has a width W3 of 5.5 mm.

In an alternative embodiment, the coupling portion does not include a U-shaped geometry. In such alternative embodiments, a coupling of the coupling portion of the saw blade and the slot of the coupling head of the handheld oscillating surgical saw is defined by a thickness and a width of the saw blade and a thickness and a height of the slot. In such alternative embodiments, the coupling head may include arms or a proximal face configured to contact a magnet housing. The arms or proximal face experience the magnetic field of the at least one magnet in the magnet housing.

Figure 8:
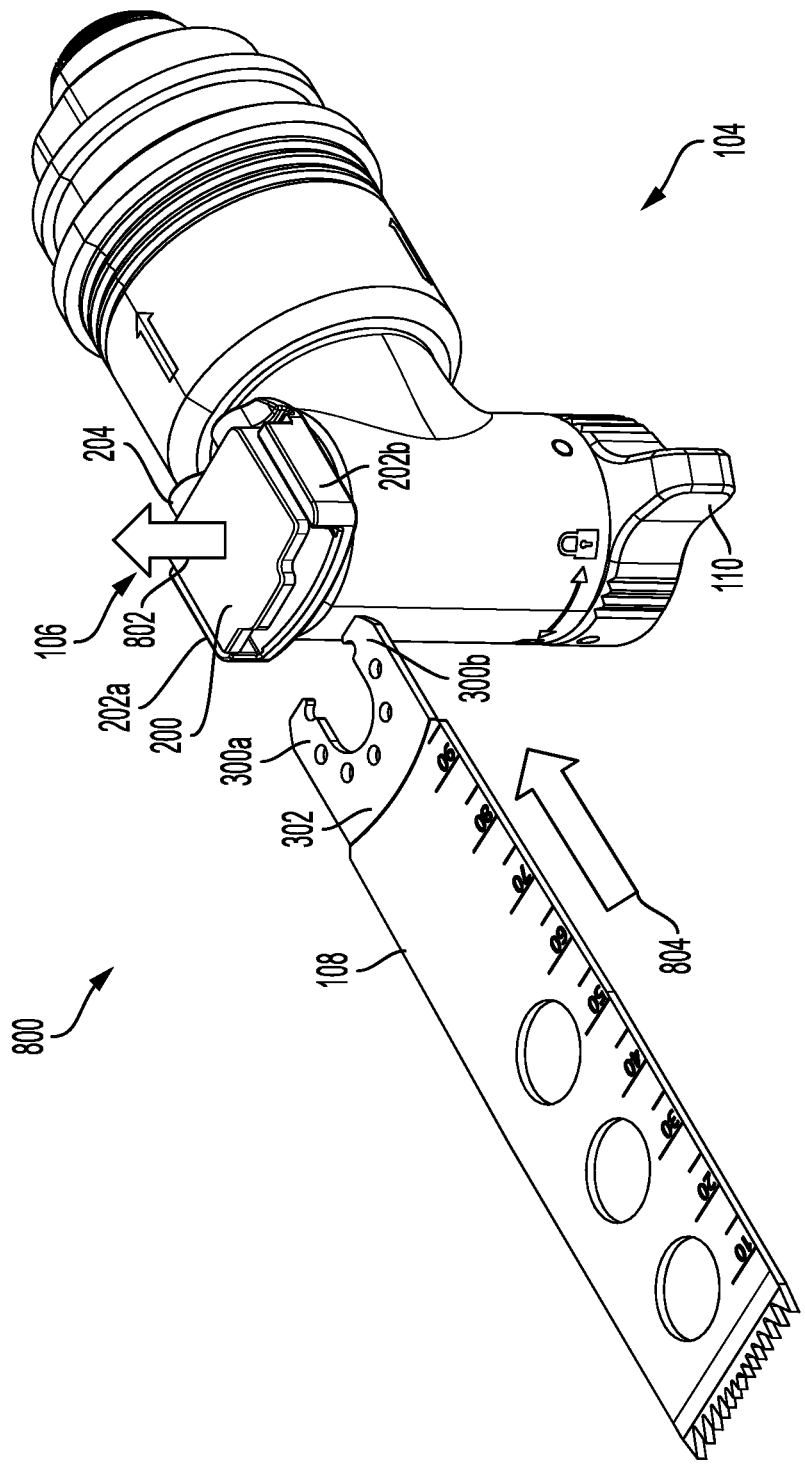
FIG. 8 is a perspective view of the saw blade and saw head of the handheld oscillating saw tool of FIG. 1 during a first step of assembly with a coupling head open and a saw blade unattached.

FIG. 8 is a perspective view of the handheld oscillating saw tool of FIG. 1 during a first stage 800 of coupling a saw blade to the coupling head 106 of the handheld oscillating surgical saw 100. First, a user ensures that the knob 110 is in an unlocked position. In the first position, the lid 200 of the coupling head 106 is raised above (represented by arrow 802) the slot 308 such that the coupling portion 302 of the saw blade 108 has clearance between the lid 200 and the bottom surface 306 (shown in FIG. 3) to slide into the slot 308. In the embodiment of FIG. 8, the slot 308 opens to a height of 1.75 mm between the underside of the lid 200 and the bottom surface 306 to provide clearance to insert a saw blade 108. With the lid 200 in the first position, the user then inserts (represented by arrow 804) the coupling portion 302 of the saw blade 108 into the slot 308.

Figure 9:
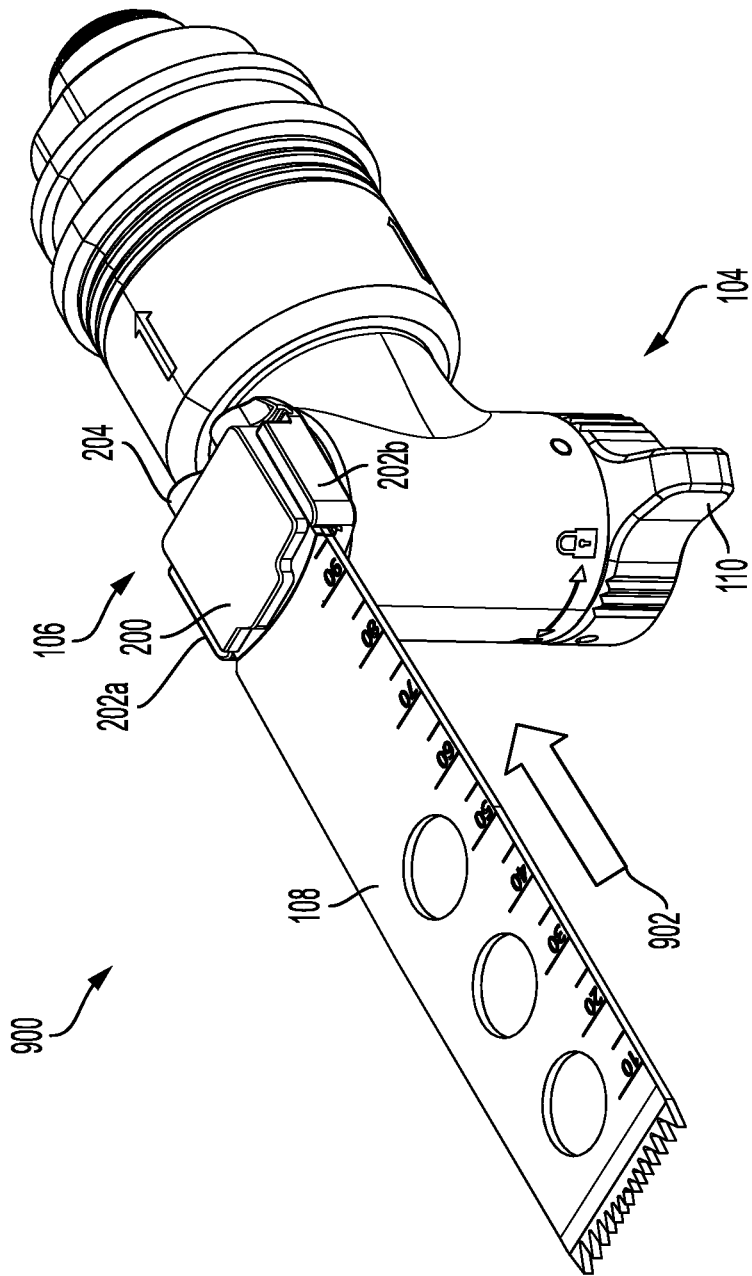
FIG. 9 is a perspective view of the saw head of the handheld oscillating saw tool of FIG. 1 during a second step of assembly with the coupling head open and the saw blade in the coupling head.

FIG. 9 is a perspective view of the handheld oscillating saw tool of FIG. 1 during a second stage of assembly 900. With the lid 200 in the first position, the user inserts the saw blade 108 into the slot 308. As the user inserts the coupling portion 302 of the saw blade 108 into the slot 308, the arms 300a, 300b of the saw blade 108 are pulled rearward (represented by arrow 902) by the magnetic force created by the magnets in the magnet housing 204. This rearward pull and contact between the arms 300a, 300b with the surface 304 provides visual, haptic, and/or audible feedback to a user that the saw blade 108 has reached the surface 304 at the rear of the slot 308.

Figure 10:
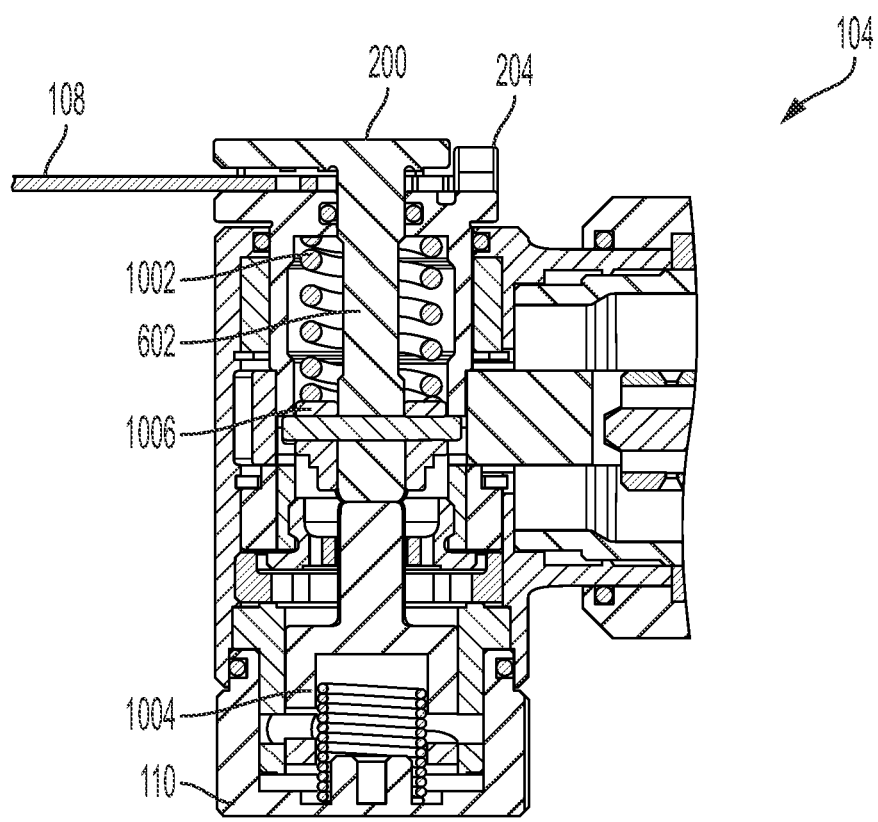
FIG. 10 is a cross sectional view of the coupling head of the handheld oscillating saw tool of FIG. 1 during the second step of assembly.

FIG. 10 is a cross-sectional view of the saw head 104 of the handheld oscillating surgical saw 100 with the lid 200 in a raised, unlocked position. In the unlocked position, the lid 200 is raised approximately 1.75 mm above the bottom surface 306 to provide clearance for inserting the saw blade 108 in the slot 308. As the knob 110 rotates between the unlocked position (shown in FIG. 10) and the locked position (shown in FIG. 14), two mechanisms provide an operative coupling between the knob 110 and the lid 200. The first mechanism raises the lid 200 as the knob 110 is turned from a locked position to the unlocked position. When moving from the locked position to the unlocked position, a pin (not shown) interacts with the knob 110 to raise a vertical piece 1004. As the vertical piece 1004 is moved upward, the vertical piece 1004 contacts the stem 602 of the lid 200 and pushes the lid 200 to an open position. The positions of the knob 110, vertical piece 1004, stem 602, and lid 200 in the unlocked position are shown in FIG. 10.

Figure 11:
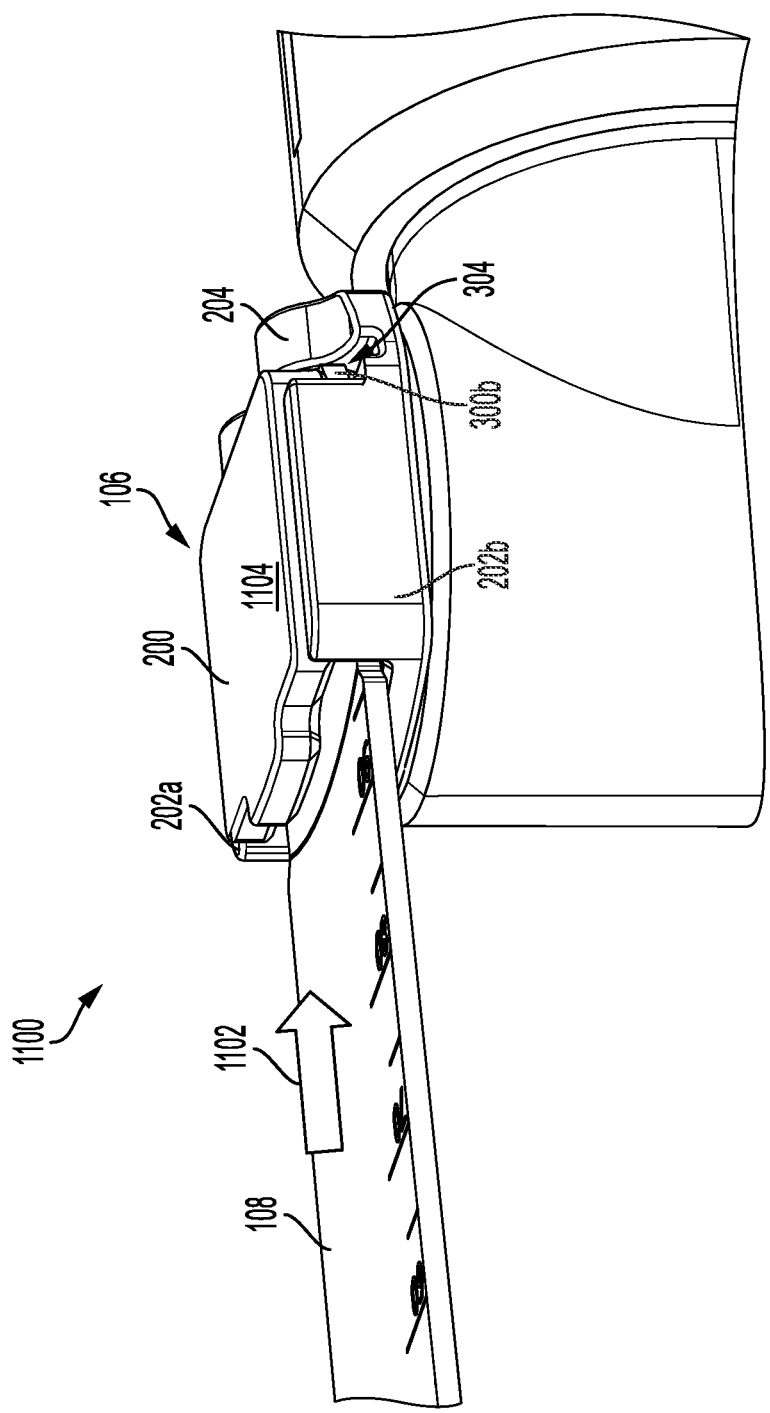
FIG. 11 is a perspective view of the coupling head of the handheld oscillating saw tool of FIG. 1 during the second stage of assembly of FIG. 9.

FIG. 11 shows a close up view 1100 of this second stage of assembly 900. A top surface 1104 of the lid 200 sits above the sidewalls 202a, 202b which indicates that the lid 200 (and the knob 110, shown in FIGS. 9-10) is in an unlocked position. As the saw blade 108 is pushed (by the user) and pulled (by the one or more magnets) rearward into the slot 308, the coupling portion 302 of the saw blade 108 is positioned within the coupling head 106. The magnetic force from the magnets in the magnet housing 204 on the saw blade 108 is sufficient to allow the saw blade 108 to be retained in the coupling head 106 when the tool is oriented with the saw blade pointing downward. This magnetic retention can be accomplished with saw blades of varying thicknesses and weights and the magnets in the magnet housing 204 may have a strength and size corresponding to the saw blades intending to be used with the tool.

The magnetic force also aids in moving the saw blade 108 into contact with the magnet housing 204 where the saw blade is position to be locked in position in the coupling head 106. In the position, the female members 404a, 404b (shown in FIG. 4) are aligned with the male member 606a, 606b on the underside 604 of the lid 200 (shown in FIG. 6).

Figure 12:
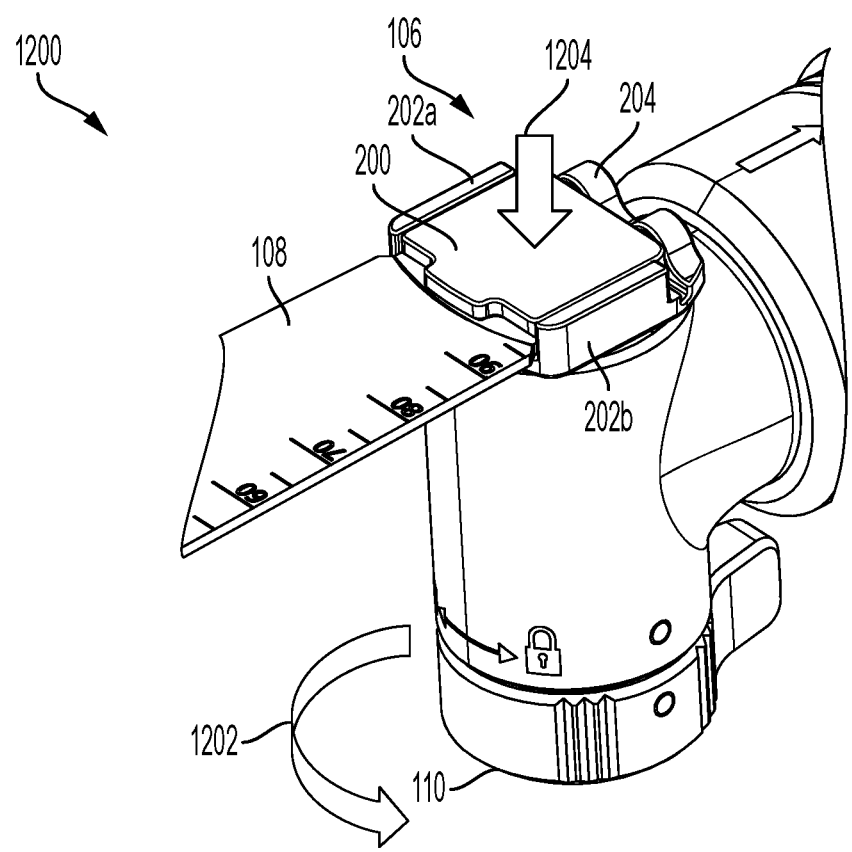
FIG. 12 is a perspective view of the saw head of the a handheld oscillating saw tool of FIG. 1 during a third stage of assembly with the saw blade locked in the coupling head.

FIG. 12 is a perspective view of the handheld oscillating saw tool of FIG. 1 during a third stage of assembly 1200. At the start of the third stage of assembly, the coupling portion 302 of the saw blade is positioned in the slot 308 and is in contact with the surface 304 of the magnet housing 204. The knob 110 is turned (represented by arrow 1202) from the unlocked position to the locked position. The turning of the knob 110 from the unlocked position to the locked position moves the lid 200 from the first position to the second position (represented by arrow 1204) and clamps the coupling portion 302 of the saw blade 108 between the bottom surface 306 of the coupling head 106 and the underside 604 of the lid 200. The male members 606a, 606b on the underside 604 of the lid 200 align with the female members 404a, 404b in the coupling portion 302 of the saw blade 108 and extend vertically within the female members 404a, 404b. This coupling of the male members 606a, 606b and the female members 404a, 404b of the coupling portion 302 of the saw blade 108 further helps to retain the saw blade 108 in place in the coupling head 106 by providing mechanical interference against pulling the saw blade 108 out of the slot 308.

Figure 13:
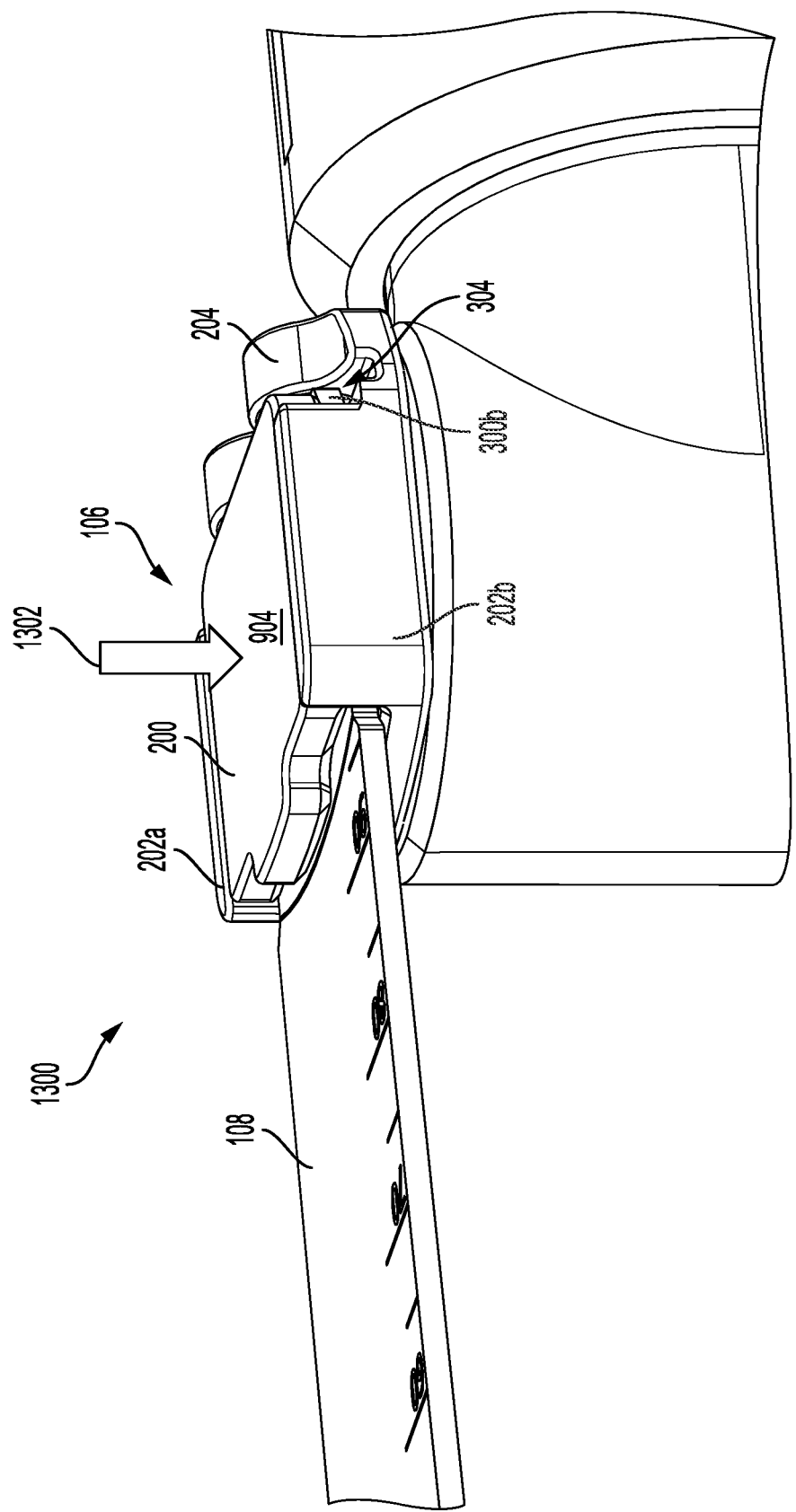
FIG. 13 is a perspective view of the coupling head of the handheld oscillating saw tool of FIG. 1 during the third stage of assembly of FIG. 12.

FIG. 13 is a close up perspective view 1300 of the coupling head of the handheld oscillating saw tool of FIG. 1 during the third stage of assembly of FIG. 12. At this stage of assembly, the lid 200 is pulled downward (represented by arrow 1302) from the first position into the second position to sandwich the coupling portion 302 of the saw blade 108 in the slot 308. As shown in FIG. 13, the top surface of the lid 200 is lower in the second position than in the first position, which is shown in the second stage of assembly depicted in FIGS. 9 and 11. In the present embodiment, the top surface 1104 of the lid 200 is even with or lower than the sidewalls 202a, 202b forming a portion of the boundary of the slot 308. After the saw blade 108 has been locked in position in the coupling head 106 as shown in FIGS. 12 and 13, the handheld oscillating saw tool is ready to be used to perform a surgical procedure.

Figure 14:
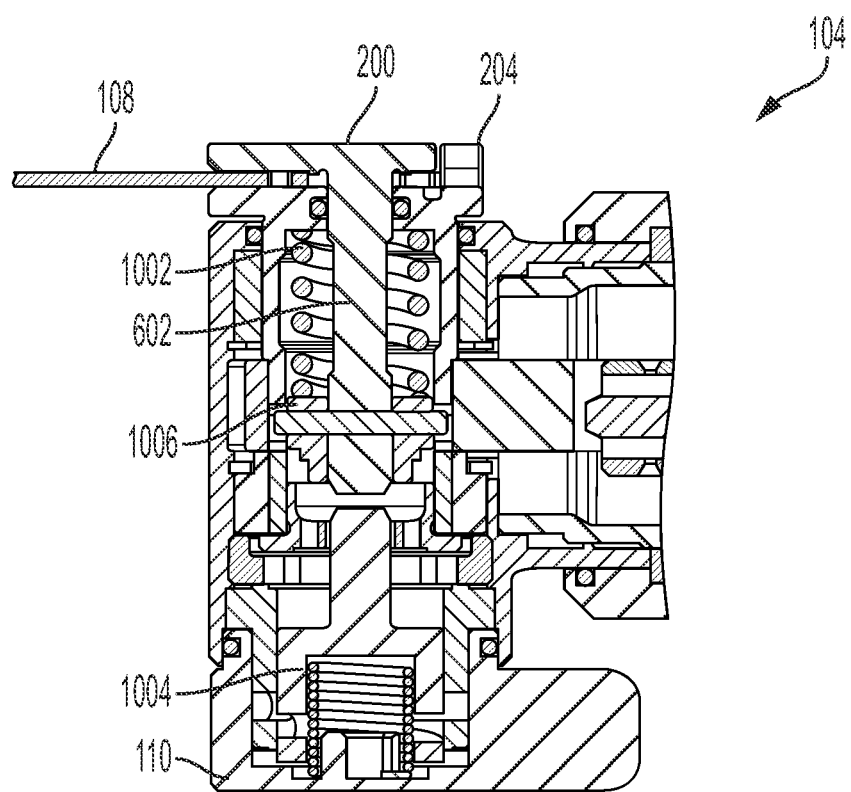
FIG. 14 is a cross sectional view of the coupling head of the handheld oscillating saw tool of FIG. 1 during the third stage of assembly.

FIG. 14 is a cross-sectional view of the saw head 104 of the handheld oscillating surgical saw 100 with the lid 200 in a lowered, locked position. As previously mentioned, as the knob 110 rotates between the unlocked position (shown in FIG. 10) and the locked position (shown in FIG. 14), two mechanisms provide an operative coupling between the knob 110 and the lid 200. The first mechanism is described above with respect to FIG. 10. The second mechanism lowers the lid 200 as the knob 110 is turned from the unlocked position to the locked position. When moving from the unlocked position to the locked position, the pin (not shown) interacting with the knob 110 moves vertical piece 1004 downward toward the knob 110 and allows a spring 1002 to expand exerting a downward force on a cylindrical piece 1006 which is coupled to the stem 602 and pulls the lid 200 downward to clamp the saw blade 108 in the slot 308. As previously discussed, when the lid 200 moves downward, the male members 606a, 606b align with the female members 404a, 404b of the coupling portion 302 of the saw blade 108 to lock the saw blade 108 in place.

Although described in the context of a handheld surgical tool, a person skilled in the art will understand that the surgical tool described herein can be used in robotic-assisted surgical applications and the like in which the handpiece is replaced by a tool housing, which in turn is coupled to a manipulator arm or another manipulated component of a robotic surgical system. In such an embodiment the saw head and coupling head will be mounted within the tool housing.

The devices disclosed herein can be designed to be disposed of after a single use, or they can be designed to be used multiple times. In either case, however, a device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation or toxic gas that can penetrate the container, such as Ethylene Oxide, gamma radiation, x-rays, or high energy electrons. The radiation kills bacteria on the instrument and in the container. The sterilized instrument can then be stored in the sterile container. The sealed container keeps the instrument sterile until it is opened in a medical facility.

Sterilization can be done by any number of ways known to those skilled in the art including beta or gamma radiation, ethylene oxide, steam, and a liquid bath (e.g., cold soak).

One skilled in the art will appreciate further features and advantages of the devices, systems, and methods based on the above-described embodiments. Accordingly, this disclosure is not to be limited by what has been particularly shown and described, except as indicated by the appended claims. All publications and references cited herein are expressly incorporated herein by reference in their entirety for all purposes.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical tool, comprising:
   a handpiece; and
   a saw head operatively coupled to the handpiece, the saw head comprising a coupling head that includes a slot and at least one magnet, the slot being configured to releasably receive a surgical saw blade configured to cut bone, and the at least one magnet being configured to magnetically attract the saw blade,
   wherein the coupling head is configured to move between a first position, in which the slot has a first height and the coupling head is configured to selectively receive the surgical saw blade therein and release the surgical saw blade therefrom, and a second position, in which the slot has a second height that is less than the first height and the coupling head is configured to fixedly seat the saw blade therein.

2. The tool of claim 1, wherein the coupling head includes a movable lid configured to be in an upward position with the coupling head in the first position and in a downward position with the coupling head in the second position.

3. The tool of claim 2, further comprising an actuator configured to be actuated to selectively cause the lid to move between the first and second positions.

4. The tool of claim 2, wherein the lid includes at least one male member extending therefrom that is configured to, with the coupling head in the second position, engage at least one corresponding female member formed in the saw blade.

5. The tool of claim 1, further comprising an actuator configured to be actuated to selectively cause the coupling head to move between the first and second positions.

6. The tool of claim 1, wherein the slot is defined by a bottom surface, a top surface, a left sidewall, a right sidewall, and a distal-facing surface;
   the at least one magnet is positioned at the distal-facing surface; and
   the saw blade is configured to extend distally out of the slot.

7. The tool of claim 6, wherein the top surface is defined by a lid configured to be movable relative to the distal-facing surface to move the coupling head between the first and second positions.

8. The tool of claim 1, wherein the coupling head moving into the second position from the first position is configured to provide feedback to a user indicative of the saw blade being fixedly seated therein, the feedback including at least one of visual feedback, audible feedback, and haptic feedback.

9. The tool of claim 8, wherein the feedback includes at least the visual feedback;
   the tool further comprises the saw blade; and
   the saw blade includes an alignment feature configured to align with the coupling head with the coupling head being in the second position.

10. The tool of claim 8, wherein the feedback includes at least the audible feedback;
the tool further comprises the saw blade; and
magnetic engagement of the saw blade and the magnet is configured to provide the audible feedback.

11. The tool of claim 8, wherein the feedback includes at least the haptic feedback;
the tool further comprises the saw blade; and
an interaction between a magnetic field produced by the magnet and the saw blade is configured to provide the haptic feedback.

12. The tool of claim 1, further comprising the saw blade;
wherein the at least one magnet includes a first magnet and a second magnet;
the saw blade includes a U-shaped proximal portion including first and second arms; and
with the coupling head in the second position, the first arm is positioned adjacent to the first magnet and the second arm is positioned adjacent to the second magnet.

13. A surgical method, comprising:
inserting a surgical saw blade into a slot formed between a base and a lid of a coupling head of a surgical tool;
sliding the saw blade proximally into the slot until the saw blade contacts a distal wall of the base and engages at least one magnet at the distal wall; and
closing the lid of the coupling head and thereby securing the saw blade to the coupling head.

14. The surgical method of claim 13, wherein the saw blade engaging the at least one magnet provides at least one of visual, audible, and haptic feedback to a user.

15. The surgical method of claim 13, wherein closing the lid of the coupling head comprises clamping the lid on the saw blade.

16. The method of claim 13, wherein closing the lid comprises actuating an actuator of the surgical tool that causes the lid to move relative to the base.

17. The method of claim 13, wherein closing the lid comprises engaging at least one male member extending from the lid with at least one corresponding female member formed in the saw blade.

18. The method of claim 16, further comprising, after closing the lid, actuating the actuator again, thereby causing the lid to move relative to the base, and then removing the saw blade from the slot.

19. The method of claim 17, wherein the saw blade cannot be removed from the slot until an actuator is actuated again.

20. The surgical method of claim 13, further comprising, with the saw blade secured to the coupling head, oscillating the saw blade relative to bone.

* * * * *